United States Patent [19]

Parrinello et al.

[11] Patent Number: 5,047,546

[45] Date of Patent: Sep. 10, 1991

[54] OXAZOLIDINES CONTAINING SILANE GROUPS

[75] Inventors: Giovanni Parrinello, Duisburg, Belgium; Rolf Mülhaupt, Marly, Switzerland; Hubert Simon, Mulhouse, France

[73] Assignee: Ciba-Geigy Corporation, Ardsley, N.Y.

[21] Appl. No.: 612,737

[22] Filed: Nov. 9, 1990

Related U.S. Application Data

[63] Continuation of Ser. No. 457,453, Dec. 27, 1989, abandoned.

[30] Foreign Application Priority Data

Dec. 29, 1988 [CH]  Switzerland ................... 4845/88

[51] Int. Cl.$^5$ ............................................. C07F 7/18
[52] U.S. Cl. ................................... 548/110; 544/222
[58] Field of Search ..................... 548/110; 544/222

[56] References Cited

U.S. PATENT DOCUMENTS 3,743,626  7/1973  Emmons .................. 260/77.5 AQ
4,772,716  9/1988  Mülhaupt et al. ................. 548/110

FOREIGN PATENT DOCUMENTS 3414877  10/1985  Fed. Rep. of Germany .

*Primary Examiner*—Richard L. Raymond
*Attorney, Agent, or Firm*—Luther A. R. Hall

[57] ABSTRACT

Compounds of the general formula I

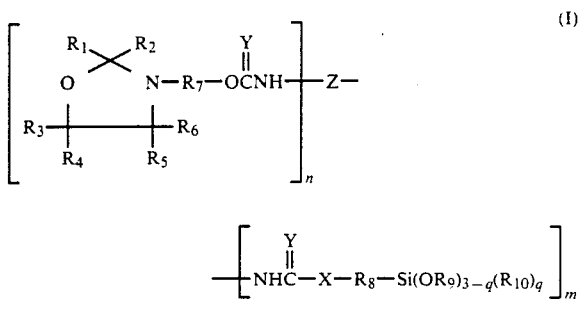

wherein
$R_1$ is a hydrogen, $C_1$–$C_{12}$alkyl, $C_5$–$C_7$cycloalkyl, phenyl or benzy.,
$R_2$ is hydrogen or $C_1$–$C_4$alkyl, or
$R_1$ and $R_2$, together with the linking carbon atom, form a 5- or 6-membered ring, and
$R_3$, $R_4$, $R_5$ and $R_6$ are identical or different and are hydrogen, $C_1$–$C_{12}$alkyl, phenyl or phenyl substituted by 1 to 3 members selected from the group consisting of $C_1$–$C_4$alkyl, halogen or $C_1$–$C_4$alkoxy or are a group of formula —$CH_2OR_{11}$, where $R_{11}$ is $C_1$–$C_{12}$alkyl, phenyl or phenyl substituted by 1 to 3 members selected from the group consisting of $C_1$–$C_4$alkyl, halogen or $C_1$–$C_4$alkoxy, or are —C(O)-$R_{12}$, and $R_{12}$ is $C_1$–$C_{12}$alkyl,
$R_7$ is $C_1$–$C_4$alkylene, $R_8$ is $C_1$–$C_8$alkylene, $R_9$ is $C_1$–$C_4$alkyl, or two radicals $R_9$ together are $C_1$–$C_4$alkylene, and $R_{10}$ is $C_1$–$C_4$alkyl or phenyl,
q is a value from 0 to 2,
X is —S— or —NH—,
Y is O or S, and
Z is an organic radical which is derived from a polyisocyanate or a polyisothiocyanate containing at least three three NCO or NCS groups respectively,
n is a value $\geq 1$ and m is a value $\geq 1$, with the proviso that $n+m \geq 3$, are suitable for use as couplers, especially for moisture-curable polyurethane resins.

13 Claims, No Drawings

OXAZOLIDINES CONTAINING SILANE GROUPS

This is a continuation of application Ser. No. 457,453, filed on Dec. 27, 1989, now abandoned.

The present invention relates to novel 1,3-oxazolidines containing silane groups, to their preparation, to the use thereof as adhesion-promoters, and to single component or two-component polyurethane resins which contain said adhesion-promoters and are used as adhesives, sealing compounds, coating compositions or insulating materials.

1,3-Oxazolidines are disclosed in U.S. Pat. No. 3,743,626 as curing agents for moisture-curable polyurethane prepolymers.

Such prepolymers are known in the art as components of adhesives, sealing compounds, coating compositions or insulating materials. The curability of these prepolymers is based on their content of free isocyanate groups, such that curing is effected under the action of moisture. Adhesion of the cured polyurethanes to glass or metal is unsatisfactory in many technical applications, and this shortcoming led to the use of primers. The use of a primer results in a good bond being formed between polyurethane and glass or metal. This bond is little affected by high humidity, elevated temperature and high mechanical stress. Useful primers are typically aminoalkylalkoxy silanes (q.v. Pluedemann et al, Silane Coupling Agents", Plenum Press, N.Y. [1982]). However, the most effective aminosilane adhesion-promoters may not be used in unmodified form as adhesion-promoters for incorporation in moisture-curable polyurethanes, as the amino groups react with isocyanate groups. For this reason German Offenlegungsschrift 3 414 877 discloses ketimines and aldimines of aminosilanes which can be added to polyurethane adhesives without adversely affecting their shelf-life.

Further, U.S. Pat. No. 4,772,716 teaches the use of 1,3-oxazolidines containing silane groups as adhesion-promoters for moisture-curable epoxy or polyurethane resins.

Lower functional oxazolidine adhesion-promoters for polyurethanes effect good bonding to glass without primer treatment, but a reduced curing rate is often observed.

A class of compounds has now been found which can be added to single component or two-component polyurethane adhesives, sealing compounds, paints and insulating materials, such that significantly enhanced bonding to glass, metal, resin-coated steel and plastics materials is achieved without the curing rate being adversely affected or even increased.

The present invention relates to compounds of general formula I

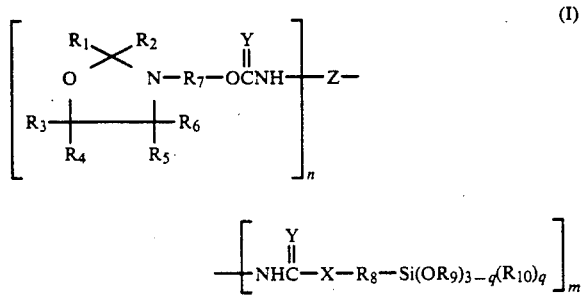

wherein $R_1$ is hydrogen, $C_1$-$C_{12}$alkyl, $C_5$-$C_7$-cycloalkyl, phenyl or benzyl, $R_2$ is hydrogen or $C_1$-$C_4$alkyl, or $R_1$ and $R_2$, together with the linking carbon atom, form a 5- or 6-membered ring, and $R_3$, $R_4$, $R_5$ and $R_6$ are identical or different and are hydrogen, $C_1$-$C_{12}$alkyl, phenyl or phenyl substituted by 1 to 3 members selected from the group consisting of $C_1$-$C_4$alkyl, halogen or $C_1$-$C_4$alkoxy, or are a group of formula —$CH_2OR_{11}$, where $R_{11}$ is $C_1$-$C_{12}$alkyl, phenyl or phenyl substituted by 1 to 3 members selected from the group consisting of $C_1$-$C_4$alkyl, halogen or $C_1$-$C_4$alkoxy, or are —C(O)—$R_{12}$, and $R_{12}$ is $C_1$-$C_{12}$alkyl, $R_7$ is $C_1$-$C_4$alkylene, $R_8$ is $C_1$-$C_8$alkylene, $R_9$ is $C_1$-$C_4$alkyl, or two radicals $R_9$ together are $C_1$-$C_4$alkylene, and $R_{10}$ is $C_1$-$C_4$alkyl or phenyl, q is a value from 0 to 2, X is —S— or —NH—, Y is O or S, and Z is an organic radical which is derived from a polyisocyanate or a polyisothiocyanate containing at least three NCO or NCS groups respectively, n is a value $\geq 1$ and m is a value $\geq 1$, with the proviso that $n+m \geq 3$.

$R_1$, $R_3$, $R_4$, $R_5$, $R_6$, $R_{11}$ and $R_{12}$ as $C_1$-$C_{12}$alkyl, preferably $C_1$-$C_4$alkyl, are typically methyl, ethyl, n-propyl, isopropyl, n-butyl, isobutyl, tert-butyl, n-pentyl, n-hexyl, linear or branched octyl, nonyl, decyl, undecyl or dodecyl.

The preferred meaning of $R_3$, $R_4$, $R_5$ and $R_6$ as alkyl is methyl.

Especially preferred are compounds of formula I wherein $R_3$, $R_4$, $R_5$ and $R_6$ are hydrogen, $C_1$-$C_4$alkyl, and at most two of these radicals are phenoxymethyl, and, in particular, compounds wherein $R_3$ and $R_6$ are hydrogen and $R_4$ and $R_5$ are methyl.

Where the radicals $R_3$, $R_4$, $R_5$ and $R_6$ occur twice in compounds in which n is 2, then said two radicals preferably each have the same meaning.

$R_2$, $R_9$ and $R_{10}$ as $C_1$-$C_4$alkyl may typically be methyl, ethyl, n-propyl, isopropyl, n-butyl, isobutyl or tert-butyl.

$R_7$ and $R_9$ as $C_1$-$C_4$alkylene and $R_8$ as $C_1$-$C_8$alkylene are linear or branched alkylene, preferably linear alkylene. Typically alkylene is methylene, ethylene, propylene, trimethylene, tetramethylene, 2-methyl-1,3-trimethylene and, for $R_8$, is additionally pentamethylene, 2-methyl-1,4-tetramethylene, 3-propyl-1,3-trimethylene, 1,6-hexamethylene, 1,7-heptamethylene, 1,8-octamethylene or 2-ethyl-1,2-hexamethylene. Preferably $R_7$ and $R_9$ are ethylene and $R_8$ is $C_1$-$C_4$alkylene, most preferably trimethylene or ethylene.

$R_1$ as $C_5$-$C_7$cycloalkyl is preferably cyclopentyl or cyclohexyl.

In preferred compounds, $R_1$ and $R_2$ are hydrogen or $C_1$-$C_4$alkyl, and, more particularly, one of $R_1$ and $R_2$ is hydrogen and the other is $C_1$-$C_4$alkyl, preferably isopropyl or tert-butyl.

$R_3$, $R_4$, $R_5$, $R_6$ and $R_{11}$ as substituted phenyl are typically o-, m- or p-methylphenyl, 2,4-dimethylphenyl, 2,4,6-trimethylphenyl, p-ethylphenyl, p-tert-butylphenyl, 2-chlorophenyl or 4-methoxyphenyl.

The radical Z is derived from a polyisocyanate or polyisothiocyanate containing at least three NCO or NCS groups, respectively. This NCO- or NCS-functionality $\geq 3$ of the polyisocyanate or polyisothiocyanate is achieved by phosgenating or thiophosgenating, for example, polyamines such as amino-terminated polyether polyols to polyisocyanates or polyisothiocyanates having a functionality $\geq 3$. The polyisocyanates or polyisothiocyanates so obtained may be either used direct or first reacted with diols, polyols, dimercaptans, diamines or polyamines to NCO- or NCS-terminated prepolymers. The polyisocyanates obtainable in the following manner can also be reacted in the same way.

A further means of preparing polyisocyanates having a NCO-functionality $\geq 3$ comprises oligomerising diisocyanates. Thus, for example, diisocyanates such as hexamethylene diisocyanate may be partially hydrolysed to biuret-containing products (for example Desmodur® N100, ex Bayer).

Further, diisocyanates such as hexamethylene diisocyanate may be partially trimerised to form higher functional polyisocyanates which contain isocyanurate rings (for example Desmodur® N3200, ex Bayer).

A chain lengthening by reacting diisocyanates with polyfuntional H acid compounds having a functionality $\geq 3$, for example triols, tetrols, pentols, triamines, polyamines or polymercaptans, also results in polyisocyanates having a NCO-functionality $\geq 3$. In this case, the ratio of NCO:OH is $>1$, preferably $>3:1$, most preferably $>10:1$.

Suitable diisocyanates are aromatic as well as aliphatic, heterocyclic, monocyclic and polycyclic bifunctional isocyanate compounds. Illustrative of such compounds are toluylene diisocyanate, diphenylmethane diisocyanate, naphthylene diisocyanate, xylylene diisocyanate, hexamethylene diisocyanate, trimethylhexamethylene diisocyanate, isophorone diisocyanate or dicyclohexylmethane diisocyanate.

The parameters m and n each independently of the other have values from 1 to 49, preferably from 1 to 9, more particularly from 1 to 5 and, most preferably, are 1,2 or 3. The sum of n+m is in general 3 to 50, preferably 3 to 10 and, most preferably, 3 to 6.

The radical Z preferably has an average molecular weight Mn of $<10\,000$, most preferably Mn $<4000$.

Y is preferably 0.

Preferred compounds of formula I are those wherein Z is derived from an aliphatic, cycloaliphatic, aliphatic/aromatic, aromatic or heterocyclic polyisocyanate or polyisothiocyanate having $\geq 3$ NCO or NCS groups respectively, which radical Z may contain one or more ester, ether, urethane, thiourethane, isocyanurate, urea or biuret functions. Particularly preferred compounds of formula I are those wherein Z is derived from an aliphatic or mixed aliphatic/aromatic polyisocyanate having $\geq 3$ NCO groups, which radical Z may contain altogether one or two ester, ether, urethane, thiourethane, isocyanurate, urea or biuret functions.

If Z in compounds of formula I contains ether oxygen atoms, then such compounds may be monoethers or oligoethers, for example a group of formula

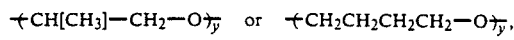

where y is an integer from 1 to 80, preferably from 1 to 20.

If Z in the compounds of formula I carries carbamate or thiocarbamate groups, then the compounds are derivatives which are obtainable by reacting polyols with compounds containing isocyanate or isothiocyanate groups. The radical Z will also be understood as including radicals which contain one or more urethane groups as well as one or more thiourea groups, for example those which contain a linking group of formula

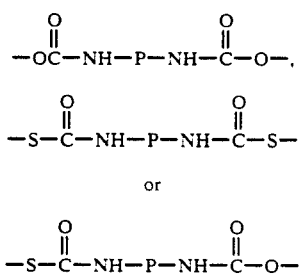

wherein P is the radical of the polyol.

Hydroxyl-terminated polyethers or polyesters may also be suitably used as polyols.

In preferred compounds of formula I, the radical Z contains two ester, carbamate, isocyanurate, urea or biuret functions, and, in particularly preferred compounds, contains one such function. The ether functions are by way of being an exception here, as they are able—as mentioned above—to form oligoether linking groups. Such compounds may therefore contain up to 80, preferably up to 20, ether functions.

Especially preferred compounds of formula I are those wherein $R_1$ is $C_1$-$C_4$alkyl, preferably isopropyl or tert-butyl, $R_2$ is hydrogen, $R_3$, $R_4$, $R_5$ and $R_6$ are each hydrogen, and $R_7$ is ethylene, and n is 1 or 2.

Also especially preferred are compounds of formula I wherein X is —S—, $R_8$ is $C_1$-$C_4$-alkylene, preferably trimethylene, and $R_9$ is $C_1$-$C_4$alkyl, preferably methyl or ethyl, and q is O. The most preferred compound of formula I is that wherein $R_1$ is isopropyl, $R_2$, $R_3$, $R_4$, $R_5$ and $R_6$ are each hydrogen, $R_7$ is ethylene, $R_8$ is trimethylene, $R_9$ is methyl, Y is O, X is —S— and Z is

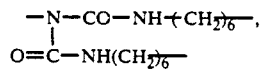

and m is 2, n is 1 and q is 0.

Illustrative of compounds of formula I are:

5,047,546

| n | R$_1$ | R$_2$ | R$_3$ | R$_6$ | R$_7$ | m | X | Y | R$_8$ | R$_9$ | q | R$_{10}$ | Z |
|---|---|---|---|---|---|---|---|---|---|---|---|---|---|
| 1 | H | $-\overset{CH_3}{\underset{|}{CH}}-CH_3$ |  | H | $-\overset{CH_3}{\underset{|}{CH}}-CH_2-$ | 2 | S | O | $+CH_2\!\!+_3$ | $-CH_3$ | 0 | — | $+CH_2\!\!+_6-N-\overset{O}{\overset{\|}{C}}-NH+CH_2\!\!+_6$<br>$\quad\quad\quad\quad\quad\; \|$<br>$\quad\quad\quad\quad O=C-NH+CH_2\!\!+_6$ |
| 2 | $-CH_2-CH_2-CH_2-CH_2-$ | $-CH_3$ | $-CH_3$ | $-CH_3$ | $-CH_2-CH_3-$ | 2 | S | O | $+CH_2\!\!+_3$ | $-CH_2-CH_3-$ | 0 | — | $\left[+CH_2\!\!+_6-NHC-O-CH_2\right]_4 C$ |
| 2 | H | $-\overset{CH_3}{\underset{|}{CH}}-CH_3$ |  | H | $-CH_2-CH_2-$ | 1 | S | O | $+CH_2\!\!+_3$ | $-CH_3$ | 0 | — | ring structure with $+CH_2\!\!+_6$ and N-CH$_2\!\!+_6$ |
| 1 | H |  | $-CH_3$ | H | $-\overset{}{\underset{|}{CH}}-CH_2$<br>$\quad\;\;CH_3$ | 2 | NH | O | $+CH_2\!\!+_3$ | $-CH_3$ | 1 |  | $+CH_2\!\!+_6-N-\overset{O}{\overset{\|}{C}}-NH+CH_2\!\!+_6$<br>$\quad\quad\quad\quad\quad\; \|$<br>$\quad\quad\quad\quad O=C-NH+CH_2\!\!+_6$ |
| 4 | H | $-\overset{CH_3}{\underset{|}{CH}}-CH_3$ |  | H | $-CH_2-CH_2-$ | 4 | S | O | $+CH_2\!\!+_3$ | $-CH_3$ | 0 | — | complex bis-hydantoin/phosphonate structure with P linker |

P: $-OCH_2-\overset{CH_3}{\underset{|}{CH}}-CH_2+OCH_2-\overset{CH_3}{\underset{|}{CH}}+_{18}O-$ Compounds are meant in which R$_4$ and R$_5$ are hydrogen.

The compounds of formula I are prepared in a manner which is known per se. The preparation can be most simply illustrated by means of the following reaction scheme:

I. Oxazolidine component

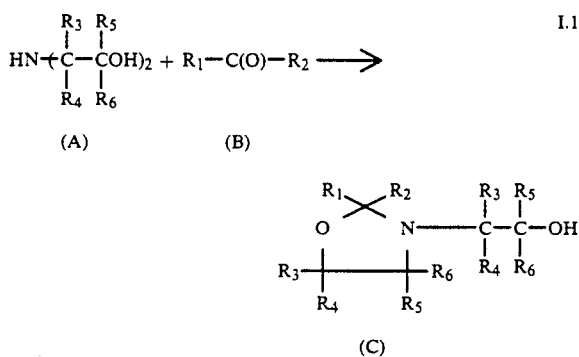

This method follows that disclosed in German Offenlegungsschrift 2 426 438. The educts (A) and (B) are known compounds, some of which are commercially available or can be prepared in simple known manner. Suitable educts (A) are especially bis(2-hydroxyethyl)amine and bis(2-hydroxypropyl)amine. Suitable educts (B) may be the carbonyl compounds formaldehyde, acetaldehyde, propionaldehyde, butyraldehyde, isobutyraldehyde, benzaldehyde, acetone, methyl butyl ketone, cyclopentanone or cyclohexanone.

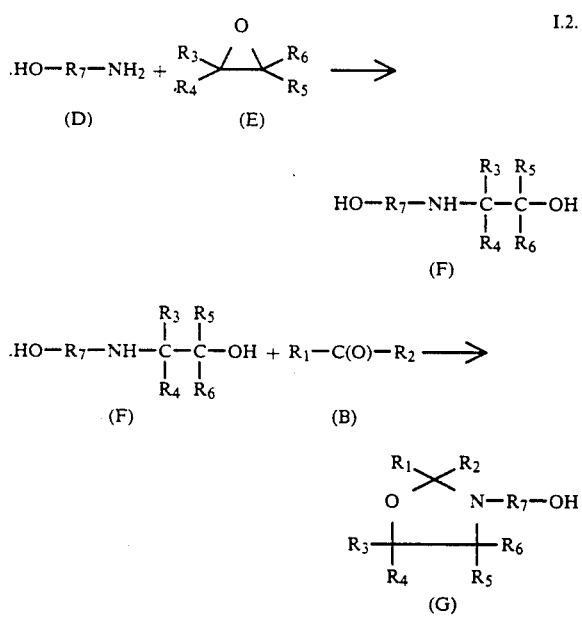

This method follows that disclosed in European patent application 096768. The educts (D), (E) and (B) are known compounds, some of which are commercially available or can be prepared in known manner. The reactive diluents customarily used in epoxy resin chemistry will preferably be used as epoxy component.

In the first step, components (D) and (E) are reacted in approximately equimolar amount in the temperature range from ca. 60°–130° C. In the second step, component (F) is reacted with the carbonyl compound (B) in the temperature range from ca. 80°–110° C., the water of reaction being removed as an azeotrope using an entrainer such as a petroleum hydrocarbon.

The resultant N-hydroxyalkyloxazolidines (C) and (G) can be reacted in further step with a polyisocyanate $Z\text{-(NCO)}_{\geq 3}$ or a polyisothiocyanate $Z\text{-(NCS)}_{\geq 3}$.

II. Silane component

The eligible amino- or mercaptoalkoxysilanes are known compounds. Some are commercially available or can be prepared by known methods. Compounds of this kind are fully described in "Silane Coupling Agents" by E. P. Pluedemann, Plenum Press, New York, 1982.

III. Polyisocyanate $Z\text{-(NCO)}_{\geq 3}$ or polyisothiocyanate $Z\text{-(NCS)}_{\geq 3}$ These components are prepared by methods which are known in the literature, for example as disclosed in: U.S. Pat. No. 3,492,330; GB patent 994,890; German patents 1 022 789, 1 222 067, 1 027 394; German Offenlegungsschrift specifications 1 929 034 and 2 004 048; U.S. Pat. No. 3,394,164; German patent 1 101 394; GB patent 889,050; Belgian patent 723 640; GB patents 956,474 and 1,072,956; U.S. Pat. No. 3,567,763; or German patent 1 231 688.

The polyisothiocyantes can be prepared in similar manner. Instead of using diisocyanates, the corresponding diisothiocyanates are used. Aliphatic educts can be prepared by the methods disclosed in U.S. Pat. No. 3,787,472, and aromatic educts by those described in Org. Syntheses; Collective Volume 1, page 447, John Wiley, New York (1948).

IV. Reaction of the polyisocyanates prepared according to III with the oxazolidines (C) and (G) and with the silanes prepared according to II to the compounds of formula I.

The reaction of the polyisocyanates or polyisothiocyanates with the other two components can be carried out in succession or simultaneously. In stepwise reaction, the oxazolidine compound (C) or (G) can first be reacted with the polyisocyanate or polyisothiocyanate respectively, and the adduct then reacted with the alkoxysilane or conversely. It is also possible in this reaction to add different oxazolidine or silane components to the polyisocyanate or polyisothiocyanate, in which case the different components can be reacted alternately, i.e. first the addition of a silane, followed by the addition of oxazolidine and, finally, addition of the second silane.

The reaction is normally carried out without a solvent, but, if required, one component or all components can be diluted with a suitable inert solvent in order to adapt, for example, the viscosity to the requirements.

The addition itself is carried out in the temperature range from 15° to 200° C., preferably from 30° to 140° C.

The reaction course can be followed by infrared spectroscopy or titration.

In the addition reactions it is also possible to use concurrently catalysts which are known per se, for example tertiary amines such as triethylamine, N-methylmorpholine, N,N,N,'N'-tetramethylethylenediamine or 1,4-diazabicyclo[2,2,2] octane. Organometallic compounds, preferably organotin compounds, may also be used as catalysts.

Illustrative of organotin compounds are tin(II) salts of carboxylic acids, for example tin(II) acetate, tin(II) octoate and tin(II) laurate, or the dialkyltin salts of carboxylic acids such as dibutyltin diacetate, dibutyltin dilaurate or dioctyltin diacetate.

The stoichiometric proportions in the addition of the oxazolidine and silane components to the polyisocyanate or polyisothiocyanate are such that the ratio of OH groups of the oxazolidines and of the $NH_2$ or SH groups of the silanes is approximately equimolar to the NCO or NCS groups of the polyisocyanates or polyisothiocyanates, respectively. The adduct may still contain free NCO or NCS groups. However, the adduct will preferably contain no free NCO or NCS groups.

With the stoichiometric ratio of the educts in the addition reaction it is possible to control the ratio of oxazolidine radicals to silane radicals in the compounds of formula I. To this end, the oxazolidine or silane compound is preferably reacted in separate steps with the polyisocyanate or polyisothiocyanate. The first step is usually carried out at a ratio of OH, $NH_2$ or SH groups to NCO or NCS groups, respectively, of less than 1. The preferred ratio of OH:NCO or NCS groups is from 1:2 to 1:6, more particularly from 1:3 to 1:5. The preferred ratio of $NH_2$ or SH:NCO or NCS groups, respectively, is from 2:3 to 1:5, more particularly from 2:3 to 1:2.

In the second step, the remaining free NCO or NCS groups are reacted with OH, $NH_2$ or SH groups. In this reaction, the stoichiometric ratio of H acid groups to NCO or NCS groups is $\geq 1$, preferably 4:1 to 1:1, most preferably 2:1 to 1:1.

It is, however, also possible in the second step to react the remaining free NCO or NCS groups only partially. In this case, the same stoichiometric ratios apply as in the first addition step. Such a procedure is preferred when two or more different oxazolidine or silane compounds are to be added.

The compounds of this invention can in principle be used as adhesion-promoters in different substrates. They are particularly effective when used in moisture-curable polyurethane resins which find utility as adhesives, sealing compounds, paints or insulating materials. When used in adhesives, the compounds of this invention have properties which enable them to be used in two-component and, most preferably, in single component systems. The use of the compounds of the invention as built-in adhesion-promoters in the cited substrates make a pretreatment of the bonding surfaces with a primer superfluous. Illustrative of such a utility is the bonding of windscreens and headlamps in automobile construction. Compounds of formula I in which $n \geq 2$, may also be used as moisture-activated hardeners for the cited substrates. Further, compounds of formula I can be used as primers for the pretreatment of substrates.

If the substrate is a moisture-curable polyurethane, then it contains as main constituent polyfunctional isocyanates and/or polyurethane prepolymers. Suitable are aromatic as well as aliphatic monocyclic and polycyclic polyfunctional isocyanate compounds. Thus in a first embodiment of the invention, toluylene diisocyanate or diphenylmethane diisocyanate may be used as aromatic isocyanate compound. Technical diphenylmethane diisocyanate having a content of higher functional diisocyanates and an isocyanate group functionality greater than 2 is especially suitable. A further suitable aliphatic diisocyanate is xylylene diisocyanate. It is further possible to use a wide range of aliphatic isocyanates having a functionality of 2 and more. In this connection, isophorone diisocyanate and dicyclohexylmethane diisocyanate are illustrative of cyclic aliphatic diisocyanates. Further examples are the aliphatic linear diisocyanates obtained by phosgenation of diamines, for example tetramethylene diisocyanate or hexamethylene diisocyanate.

A preferred embodiment of the invention comprises the use of polyurethane prepolymers instead of polyfunctional isocyanate compounds. In this context, prepolymers will be understood as meaning the adducts of an excess of polyfunctional isocyanates with polyfunctional alcohols, for example the reaction products of one of the above mentioned aromatic or aliphatic diisocyanates with ethylene glycol, propylene glycol, glycerol, trimethylolpropane or pentaerythritol. Reaction products of diisocyanates with polyether polyols, for example polyether polyols derived from polyethylene oxide or derived from polypropylene oxide can also be used. Polyurethane prepolymers derived from polyether polyols having molecular weights in the range from 200 to 10 000, preferably from 500 to 3000, are preferred. A host of such polyether polyols are known to the skilled person in the field of polyurethane chemistry. They are available from numerous suppliers and are characterised by their molecular weight (number average) which can be calculated from end group analyses. Further suitable polyether polyols are those derived from polytetrahydrofuran.

Instead of using polyether polyols it is also possible to use polyester polyols. Suitable polyester polyols are reaction products of polyfunctional acids with polyfunctional alcohols, for example polyesters derived from aliphatic and/or aromatic dicarboxylic acid and polyfunctional alcohols having a functionality of 2-4. Thus polyesters of adipic acid, sebacid acid, phthalic acid, hydrophthalic acid and/or trimellitic acid on the one hand, and ethylene glycol, propylene glycol, neopentyl glycol, hexane glycol, glycerol and/or trimethylolpropane on the other, can be used. Particularly suitable are polyester polyols having a molecular weight (number average) in the range from 500 to 5000, preferably from 600 to 2000. Further suitable polyester polyols are the polyadducts of caprolactone with alcohols having a functionality of 2-4, for example the polyadduct of 1 to 5 mol of caprolactone with 1 mol of ethylene glycol, propylene glycol, glycerol and/or trimethylolpropane.

A further suitable class of polyfunctional alcohols is that of the polybutadienols. These alcohols are oligomers derived from butadiene and contain OH end groups. Suitable products are those in the molecular weight range from 200 to 4000, preferably from 500 to 3000. Siloxane prepolymers, preferably in conjunction with other prepolymers, are also suitable.

In the preparation of the polyurethane prepolymers, the ratio of OH groups of the alcohol component to isocyanate groups is important. This ratio is usually from 1:2 to 1:10. Greater excesses of isocyanate will result in more or less low viscosity polyurethane prepolymers, whereas smaller excesses of isocyanate usually give formulations which are only spreadable with a trowel.

The polyurehane expert knows that the density of the crosslinking, and hence the brittleness of polyurethanes, increases with the functionality of the isocyanate component or also that of the polyol. Reference is made in this connection to the general technical literature, for example to the monograph of Saunders and Frisch "Polyurethanes, Chemistry and Technology", Volume XVI of the series High Polymers, Interscience Publishers, New York/London, Part I (1962) and Part II (1964).

The polyurethane formulations of this invention may additionally contain different modifiers. Fillers, for example, may be added to them. Suitable fillers are inorganic compounds which do not react with isocyanates, for example chalk or ground lime, precipitated and/or pyrogenic silicic acids, zeolites, bentonites, ground minerals as well as other inorganic fillers known to the person skilled in the art, especially ground fibres and the like. For some applications it is preferred to use fillers which impart thixotropic properties to the formulations, for example swellable plastics, preferably PVC.

In addition to containing the cited compounds, the polyurethane formulations of this invention may contain other auxiliaries such as solvents. Suitable solvents are those which do not themselves react with isocyanate groups, for example halogenated hydrocarbons, esters, ketones, aromatic hydrocarbons and the like. Plasticisers, flame retardants, retarders, colourants and ageing inhibitors conventionally added to polyurethane adhesives and sealing compounds may be incorporated in the polyurethane formulations.

For some applications it is desirable to add foam stabilisers to the polyurethane formulations of the invention. These foam stabilisers may be silicone surfactants. These surfactants are block polymers obtained from a polysiloxane block and one or more polyoxyethylene and/or polyoxypropylene blocks. The polyurethane formulations of this invention may also contain flame inhibiting and plasticising modifiers. Commonly used modifiers of this kind are those containing phosphorus and/or halogen atoms, for example tricresyl phosphate, diphenylcresyl phosphate, tris(2-chloroethyl)phosphate, tris(2-chloropropyl)phosphate and tris(2,3-dibromopropyl)phosphate. In addition it is also possible to use flame retardants, for example chlorinated paraffins, halophosphides, ammonium phosphate and resins which contain halogens and phosphorus. Further additives which may be useful for certain applications are plasticisers. Suitable plasticisers may typically be phthalates or esters of long-chain dicarboxylic acids, for example sebacates or azelates. Epoxy plasticisers such as epoxidised fatty acid derivatives may also be used.

Other possible additives are basic accelerators. Basic accelerators are typically bis(N,N-dimethylamino) diethyl ether, dimethylaminocyclohexane, N,N-dimethylbenzylamine, N-methylmorpholine as well as the reaction products of dialkyl(β-hydroxyethyl)amine with monoisocyanates and esterification products of dialkyl(β-hydroxyethyl)amine and dicarboxylic acids. Another useful accelerator is 1,4-diaminobicyclo[2,2,2]octane. It is, moreover, possible to use non-basic compounds as accelerators, for example metal compounds such as iron pentacarbonyl, nickel tetracarbonyl, iron acetylacetonate as well as tin(II) 2-ethylhexanoate, dibutyltin dilaurate or molybdenum glycolate.

The compounds of formula I are added to polyurethane prepolymers in an amount of 0.1–20% by weight, more particularly 0.5–5% by weight and, most preferably, 0.5–2.5% by weight, based on the prepolymer.

If the compounds of formula I are used as hardener, then the molar ratio of liberated >NH groups to free isocyanate groups in the prepolymer is is 0.5 to 1.5:1, preferably 0.9 to 1.11:1.

EXAMPLE 1

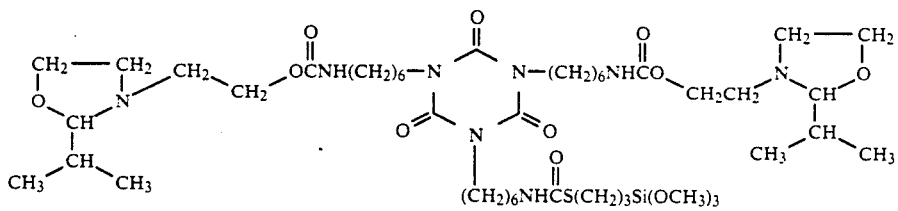

A mixture of 50 g of partially trimerised hexamethylene diisocyanate having an isocyanate content of 21.6% (Desmodur ® N3200, ex Bayer AG) and 16.8 g of 3-mercaptopropyltrimethoxysilane is heated for 60 minutes at 140° C. until the isocyanate content is 10.4%. The mixture is then cooled to 100° C. and to it is added a mixture of 27.2 g of N-(2-hydroxyethyl)-2-isopropylidene-1,3-oxazolidine (b.p. 54° C./13.3 Pa; prepared from isobutyraldehyde and diethanolamine) and 100 ml of dry toluene, and the reaction mixture is stirred for 1 hour at 100° C. until no more free isocyanate is detectable. The toluene is then stripped off on a rotary evaporator at 95° C./17.3 kPa, giving 93 g (98%) of a viscous resin for which the following analytical date are obtained:

Viscosity (according to Epprecht): $\eta_{40}$=181 760 mPa.s

Amine content (titration): 1.73 mol NR$_3$/kg (cal. 1.96)

| Elemental analysis: | found | calculated | for $C_{46}H_{86}N_8O_{13}SSi$ |
|---|---|---|---|
| % C | 54.80 | 54.36 | |
| % H | 8.74 | 8.74 | |
| % N | 11.90 | 11.03 | |
| % S | 2.98 | 3.12 | |

EXAMPLE 2

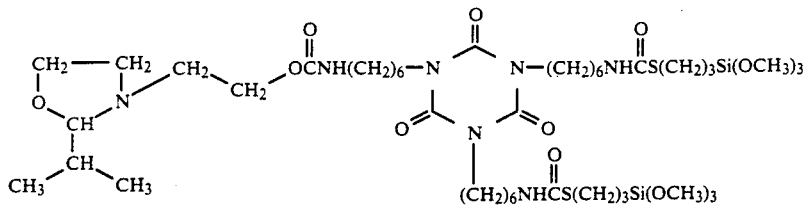

A mixture of 45 g of partially trimerised hexamethylene diisocyanate having an isocyanate content of 21.6% (Desmodur® N3200, ex Bayer AG) and 30.3 g of 3-mercaptopropyltrimethoxysilane is heated for 60 minutes at 140° C. until the isocyanate content is 4.0%. The mixture is then cooled to 100° C. and to it is added a mixture of 12.2 g of N-(2-hydroxyethyl)-2-isopropylidene-1,3-oxazolidine (b.p. 54° C./13.3 Pa; prepared from isobutyraldehyde and diethanolamine) and 100 ml of dry toluene, and the reaction mixture is stirred for 1 hour at 100° C. until no more free isocyanate is detectable. The toluene is then stripped off on a rotary evaporator at 95° C./17.3 kPa, giving 83.5 g (95%) of a viscous resin for which the following analytical date are obtained:

Viscosity (according to Epprecht):$\eta_{40}$=353 280 mPa.s

Amine content (titration): 0.81 mol $NR_3$/kg (cal. 0.94)

| Elemental analysis: | found | calculated | for $C_{44}H_{85}N_7O_{14}S_2Si_2$ |
|---|---|---|---|
| % C | 50.75 | 50.02 | |
| % H | 8.74 | 8.11 | |
| % N | 10.31 | 9.28 | |
| % S | 5.85 | 6.07 | |

EXAMPLE 3

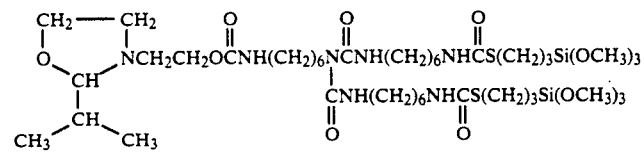

A mixture of 50 g of biuret-containing partially hydrolysed hexamethylene diisocyanate having an isocyanate content of 21.3% (Desmodur® N100, ex Bayer AG) and 33.5 g of 3-mercaptopropyltrimethoxysilane is heated for 60 minutes at 140° C. until the isocyanate content is 4.5%. The mixture is then cooled to 100° C. and to it is added a mixture of 13.5 g of N-(2-hydroxyethyl)-2-isopropylidene-1,3-oxazolidine (b.p. 54° C./13.3 Pa; prepared from isobutyraldehyde and diethanolamine) and 100 ml of dry toluene, and the reaction mixture is stirred for 1 hour at 100° C. until no more free isocyanate is detectable. The toluene is then stripped off on a rotary evaporator at 95° C./17.3 kPa, giving 95.3 g (98%) of a viscous resin forwhich the following analytical data are obtained:

Viscosity (according to Epprecht):$\eta_{40}$=179 800 mPa.s

Amine content (titration): 0.93 mol $NR_3$/kg (calculated 0.97)

| Elemental analysis: | found | calculated | for $C_{43}H_{87}N_7O_{13}S_2Si_2$ |
|---|---|---|---|
| % C | 50.65 | 50.12 | |
| % H | 8.50 | 8.51 | |
| % N | 10.39 | 9.51 | |
| % S | 5.64 | 6.22 | |

EXAMPLE 4

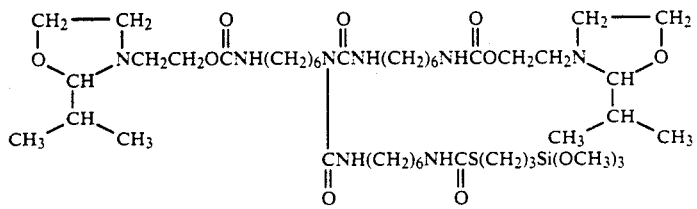

A mixture of 50 g of biuret-containing partially hydrolysed hexamethylene diisocyanate having an isocyanate content of 21.3% (Desmodur® N100, ex Bayer AG) and 16.7 g of 3-mercaptopropyltrimethoxysilane is heated for 60 minutes at 140° C. until the isocyanate content is 10.2%. The mixture is then cooled to 100° C. and to it is added a mixture of 27.0 g of N-(2-hydroxyethyl)-2-isopropylidene-1,3-oxazolidine (b.p. 54° C./13.3 Pa; prepared from isobutyraldehyde and diethanolamine) and 100 ml of dry toluene, and the reaction mixture is stirred for 1 hour at 100° C. until no more free isocyanate is detectable. The toluene is then stripped off on a rotary evaporator at 95° C./17.3 kPa, giving 91.0 g (97%) of a viscous resin for which the following analytical data are obtained:

Viscosity (according to Epprecht): $\eta_{40}$=322 360 mPa.s

Amine content (titration): 1.94 mol $NR_3$/kg (calculated 2.02)

| Elemental analysis: | found | calculated | for $C_{45}H_{88}N_8O_{12}SSi$ |
|---|---|---|---|
| % C | 54.81 | 54.44 | |
| % H | 8.82 | 8.87 | |
| % N | 11.93 | 11.29 | |
| % S | 2.97 | 3.22 | |

EXAMPLE 5

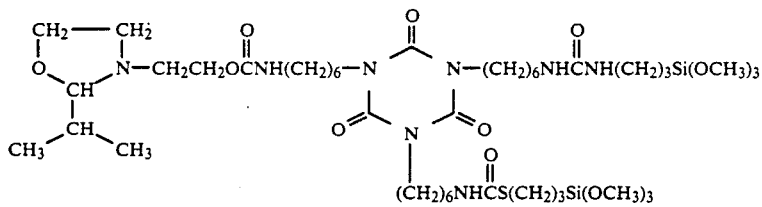

To 50 g of partially trimerised hexamethylene diisocyanate having an isocyanate content of 21.6% (Desmodur® N3200, ex Bayer AG) are added 16.8 g of 3-mercaptopropyltrimethoxysilane and the mixture is heated for 60 minutes at 140° C. until the isocyanate content is 10.7%. The mixture is then cooled to 100° C. and to it are added dropwise 13.6 g of N-(2-hydroxyethyl)-2-isopropylidene-1,3-oxazolidine (b.p. 54° C./13.3 Pa; prepared from isobutyraldehyde and diethanolamine), and the reaction mixture is stirred for 30 minutes at 100° C. until the isocyanate content is 2%. After cooling to 40° C., 15.3 g of aminopropyltrimethoxysilane are added and stirring is continued for 1 hour until no more isocyanate is detectable, affording a viscous isocyanate-free resin for which the following analytical data are obtained:

Viscosity (according to Epprecht): $\eta_{80}=5760$ mPa.s
Amine content (titration): 0.90 mol $NR_3$/kg (cal. 0.96 mol $NR_3$/kg)

| Elemental analysis: | found | calculated | for $C_{44}H_{86}N_8O_{14}SSi_2$ |
|---|---|---|---|
| % C | 51.21 | 50.87 | |
| % H | 8.70 | 8.29 | |
| % N | 11.38 | 10.80 | |
| % S | 2.56 | 3.08 | |

EXAMPLE 6

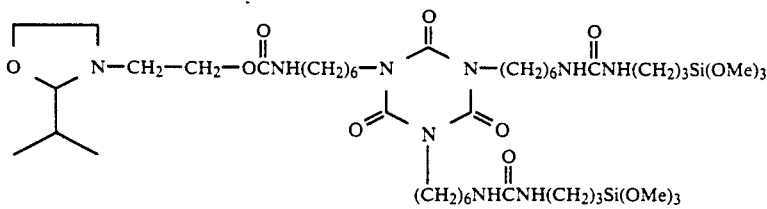

To 50 g of partially trimerised hexamethylene diisocyanate having an isocyanate content of 21.6% (Desmodur® N3200, ex Bayer AG) are added 13.6 g of N-(2-hydroxyethyl)-2-isopropylidene-1,3-oxazolidine (b.p. 54° C./13.3 Pa; prepared from isobutyraldehyde and diethanolamine), and the reaction mixture is stirred for 60 minutes at 100° C. until the isocyanate content is 9%. After cooling, 30.6 g of aminopropyltrimethoxysilane are added at 30° C. and stirring is continued for 1 hour until no more isocyanate is detectable, affording a viscous isocyanate-free resin for which the following analytical date are obtained:

Viscosity (according to Epprecht): $\eta_{80}=18080$ mPa.s
Amine content (titration): 0.92 mol $NR_3$/kg (cal. 0.97 mol $NR_3$/kg)

| Elemental analysis: | found | calculated | for $C_{44}H_{87}N_9O_{14}Si_2$ |
|---|---|---|---|
| % C | 52.47 | 51.71 | |
| % H | 8.90 | 8.52 | |
| % N | 12.85 | 12.34 | |

EXAMPLE 7

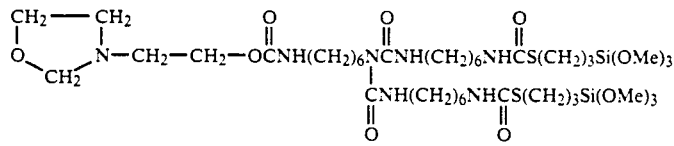

A mixture of 156 g of biuret-containing partially hydrolysed hexamethylene diisocyanate having an isocyanate content of 21.3% (Desmodur® N100, ex Bayer AG) and 110 g of 3-mercaptopropyltrimethoxysilane is heated for 60 minutes at 140° C. until the isocyanate content is 2.8%. The mixture is then cooled to 100° C. and to it are added 31 g of N-(2-hydroxyethyl)-1,3-oxazolidine (b.p. 99° C./700 Pa; prepared from paraformaldehyde and diethanolamine) and 100 ml of dry toluene, and the reaction mixture is stirred for 1 hour at 100° C. until no more free isocyanate is detectable. The toluene is then stripped off on a rotary evaporator at 95° C./17.3 kPa, giving 290 g (97%) of a viscous resin for which the following analytical date are obtained:

Viscosity (according to Epprecht): $\eta_{40}=197120$ mPa.s

Amine content (titration): 0.89 mol NR₃/kg (calculated 1.00)

| Elemental analysis: | found | calculated | for C₄₀H₈₁N₇O₁₃S₂Si₂ |
|---|---|---|---|
| % C | 49.22 | 48.61 | |
| % H | 8.18 | 8.26 | |
| % N | 10.51 | 9.92 | |
| % S | 6.04 | 6.49 | |

EXAMPLE 8

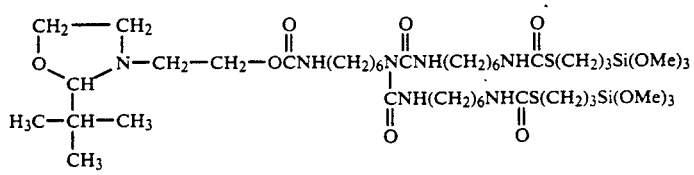

A mixture of 160.6 g of biuret-containing partially hydrolysed hexamethylene diisocyanate having an isocyanate content of 21.3% (Desmodur® N100, ex Bayer AG) and 107.6 g of 3-mercaptopropyltrimethoxysilane is heated for 1 hour at 140° C. until the isocyanate content is 2.8%. The mixture is then cooled to 100° C. and to it are added 47.3 g of N-(2-hydroxyethyl)-2-(tert-butyl)-1,3-oxazolidine (b.p. 112° C./700 Pa; prepared from pivalaldehyde and diethanolamine) and 100 ml of dry toluene, and the reaction mixture is stirred for 1 hour at 100° C. until no more free isocyanate is detectable. The toluene is then stripped off on a rotary evaporator at 95° C./17.3 kPa, giving 289 g (92%) of a viscous resin for which the following analytical date are obtained:

Viscosity (according to Epprecht): $\eta_{80}=6720$ mPa.s

Amine content (titration): 0.83 mol NR₃/kg (calculated 0.95)

| Elemental analysis: | found | calculated | for C₄₄H₈₈N₇O₁₃S₂Si₂ |
|---|---|---|---|
| % C | 51.16 | 50.64 | |
| % H | 8.51 | 8.50 | |
| % N | 10.21 | 9.40 | |
| % S | 5.72 | 6.14 | |

EXAMPLE 9

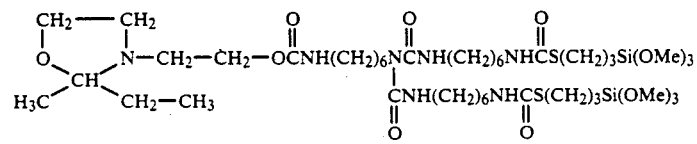

A mixture of 200 g of biuret-containing partially hydrolysed hexamethylene diisocyanate having an isocyanate content of 21.3% (Desmodur® N100, ex Bayer AG) and 134 g of 3-mercaptopropyltrimethoxysilane is heated for 1 hour at 140° C. until the isocyanate content is 2.8%. The mixture is then cooled to 100° C. and to it are added 54.1 g of N-(2-hydroxyethyl)-2-methyl-2-ethyl-1,3-oxazolidine (b.p. 114° C./500 Pa; prepared from methyl ethyl ketone and diethanolamine) and 100 ml of dry toluene, and the reaction mixture is stirred for 1 hour at 100° C. until no more free isocyanate is detectable. The toluene is then stripped off on a rotary evaporator at 95° C./17.3 kPa, giving 380 g (98%) of a viscous resin for which the following analytical date are obtained:

Viscosity (according to Epprecht): $\eta_{80}=18560$ mPa.s

Amine content (titration): 0.88 mol NR₃/kg (calc. 0.97)

| Elemental analysis: | found | calculated | for C₄₃H₈₇N₇O₁₃S₂Si₂ |
|---|---|---|---|
| % C | 50.63 | 50.12 | |
| % H | 8.58 | 8.51 | |
| % N | 10.26 | 9.51 | |
| % S | 5.67 | 6.22 | |

EXAMPLE 10

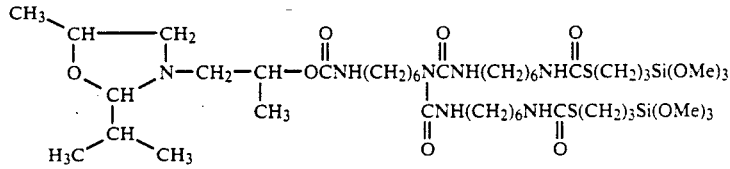

A mixture of 200 g of biuret-containing partially hydrolysed hexamethylene diisocyanate having an isocyanate content of 21.3% (Desmodur®N100, ex Bayer AG) and 141 g of 3-mercaptopropyltrimethoxysilane is heated for 1 hour at 140° C. until the isocyanate content is 2.8%. The mixture is then cooled to 100° C. and to it are added 63.5 g of N-(2-hydroxy-2-methylethyl)-2-isopropylidene-4-methyl-1,3-oxazolidine (b.p. 103° C./700 Pa; prepared from isobutyrylaldehyde and bis(2-hydroxypropyl)amine) and 100 ml of dry toluene, and the reaction mixture is stirred for 1 hour at 100° C. until no more free isocyanate is detectable. The toluene is then stripped off on a rotary evaporator at 95° C./17.3 kPa, giving 400 g (98%) of a viscous resin for which the following analytical date are obtained:

Viscosity (according to Epprecht): $\eta_{40}=55680$ mPa.s

Amine content (titration): 0.86 mol NR₃/kg (calc. 0.94)

| Elemental analysis: | found | calculated | for $C_{45}H_{91}N_7O_{13}S_2Si_2$ |
|---|---|---|---|
| % C | 51.19 | 51.06 | |
| % H | 8.59 | 8.67 | |
| % N | 9.91 | 9.26 | |
| % S | 6.04 | 6.06 | |

EXAMPLE 11

Oxazolidine- and mercaptosilane-terminated prepolymer

To 100 g of partially trimerised hexamethylene diisocyanate having an isocyanate content of 21.6% (Desmodur® N100, ex Bayer AG) are added 50 g of dry bishydroxyl-terminated polypropylene glycol having a molecular weight of 1000 (Desmophen® 1600 U, ex Bayer AG) at 100° C. The reaction mixture is then stirred at 140° C. for 2 hours until the isocyanate content is 11.5%. To this mixture are added 53.8 g of 3-mercaptotrimethoxysilane, and the batch is stirred until the isocyanate content is 2.5%. Then 21.8 g of N-(2-hydroxyethyl)-2-isopropylidene-1,3-oxazolidine, whereupon the mixture is stirred for 2 hours until no more free isocyanate is detectable.

Viscosity (according to Epprecht): $\eta_{40}$=373 760 mPa.s

Amine content (titration): 0.697 mol $NR_3$/kg.

EXAMPLE 12

A) Prepolymer synthesis:

An isocyanate-terminated prepolymer is prepared by running a mixture of 531 g of dry bishydroxyl-terminated polypropylene glycol having a molecular weight of 2000 (Desmophen® 1900 U, ex Bayer AG) and 0.3 ml of dibutyltin dilaurate at 80° C. into 150 g of methylenediphenyl diisocyanate (Isonate® 125M, ex Upjohn) over the course of 1 hour. Then 2.7 g of trimethylolpropane are added, and the mixture is stirred for 2 hours at 80° C. until an isocyanate-terminated prepolymer having an isocyanate content of 2.7% has formed.

B) Adhesion to glass:

To 137 g of this prepolymer are added 6.8 g of dry pyrogenic silica (Aerosil 380) and an oxazolidine-silane adhesion-promoter of Table 1. Then a 4 mm thick polyurethane layer is cast on a glass plate. After 2 weeks these samples are stored in water for 2 weeks at room temperature. The results are summarised in Table 1, in which (−) indicates that the polyurethane layer has become completely detached, (+) that the polyurethane layer has not become detached and, when stripped off, exhibits <50% cohesive failure. (++) indicates that the polyurethane layer does not become detached and that, on being stripped off, exhibits 100% cohesive failure. In addition, the Shore A hardness according to DIN 53 505 is measured (Table 2).

TABLE 1

| Example | Adhesion-promoter of Example | Content of coupler [% by weight] | Adhesion to glass |
|---|---|---|---|
| — | — | — | — |
| A | 1 | 9.0 | + |
| B | 2 | 9.0 | + |
| C | 3 | 4.5 | ++ |
| D | 4 | 4.5 | ++ |
| E | 5 | 4.5 | + |
| F | 6 | 4.5 | ++ |
| J | 7 | 4.5 | ++ |
| K | 8 | 4.5 | ++ |
| L | 9 | 4.5 | ++ |
| M | 10 | 4.5 | ++ |

TABLE 2

| Example | Coupler of Example | Content of coupler [% by weight] | Build-up of Shore hardness A | | | | |
|---|---|---|---|---|---|---|---|
| | | | 1 | 2 | 5 | 9 | 14 [days] |
| — | — | — | 1 | 6 | 19 | 29 | 30 |
| G | 3 | 4.5 | 1 | 8.5 | 32 | 32 | 32 |
| H | 4 | 4.5 | 1 | 6 | 32 | 32 | 32 |

What is claimed is:

1. A compound of the general formula I

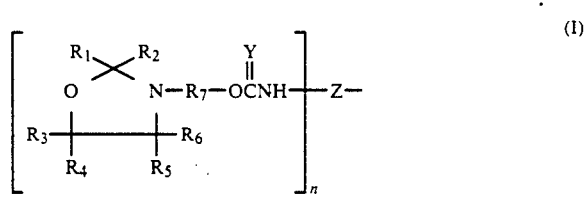

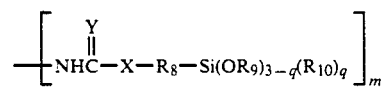

wherein
$R_1$ is hydrogen, $C_1$-$C_{12}$alkyl, $C_5$-$C_7$cycloalkyl, phenyl or benzyl,
$R_2$ is hydrogen or $C_1$-$C_4$alkyl, or
$R_1$ and $R_2$, together with the linking carbon atom, form a 5- or 6-membered ring, and
$R_3$, $R_4$, $R_5$ and $R_6$ are identical or different and are hydrogen, $C_1$-$C_{12}$alkyl, phenyl or phenyl substituted by 1 to 3 members selected from the group consisting of $C_1$-$C_4$alkyl, halogen or $C_1$-$C_4$alkoxy or are a group of formula —$CH_2OR_{11}$, where $R_{11}$ is $C_1$-$C_{12}$alkyl, phenyl or phenyl substituted by 1 to 3 members selected from the group consisting of $C_1$-$C_4$alkyl, halogen or $C_1$-$C_4$alkoxy, or are —C(O)—$R_{12}$, and $R_{12}$ is $C_1$-$C_{12}$alkyl,
$R_7$ is $C_1$-$C_4$alkylene, $R_8$ is $C_1$-$C_8$alkylene, $R_9$ is $C_1$-$C_4$alkyl, or two radicals $R_9$ together are $C_1$-$C_4$alkylene, and $R_{10}$ is $C_1$-$C_4$alkyl or phenyl,
q is a value from 0 to 2,
X is —S— or —NH—,
Y is O or S, and
Z is an organic radical which is derived from a polyisocyanate or a polyisothiocyanate containing at least three NCO or NCS groups respectively,
n is a value $\geq 1$ and m is a value $\geq 1$, with the proviso that n+m$\geq$3.

2. A compound according to claim 1, wherein Y is O.

3. A compound of formula I according to claim 1, wherein Z is derived from an aliphatic, cycloaliphatic, aliphatic/aromatic, aromatic or heterocyclic polyisocyanate or polyisothiocyanate having $\geq$3 NCO or NCS groups, which radical Z may contain one or more ester, ether, urethane, thiourethane, isocyanate, urea or biuret functions.

4. A compound of formula I according to claim 3, wherein Z is derived from an aliphatic or mixed aliphatic/aromatic polyisocyanate having $\geq 3$ NCO groups, which radical Z may contain one or two ester, ether, urethane, thiourethane, isocyanate, urea or biuret functions.

5. A compound of formula I according to claim 1, wherein the radical Z has an average molecular weight $M_n$ of $<10000$.

6. A compound of formula I according to claim 1, wherein n and m are each independently of the other integers from 1 to 49.

7. A compound of formula I according to claim 1, wherein the sum of n+m is 3 to 50.

8. A compound of formula I according to claim 1, wherein n is 1 or 2 and m is 2 or 1.

9. A compound of formula I according to claim 1, wherein $R_1$ and $R_2$ are each independently of the other hydrogen or $C_1$-$C_4$alkyl.

10. A compound of formula I according to claim 1, wherein $R_3$, $R_4$, $R_5$ and $R_6$ are hydrogen or $C_1$-$C_4$alkyl, and at most two these radicals are phenoxymethyl.

11. A compound of formula I according to claim 1, wherein $R_3$ and $R_6$ are hydrogen and $R_4$ and $R_5$ are hydrogen or methyl.

12. A compound of formula I according to claim 1, wherein $R_1$ is $C_1$-$C_4$alkyl, $R_2$ is hydrogen, $R_3$, $R_4$, $R_5$ and $R_6$ are each hydrogen, and $R_7$ is ethylene.

13. A compound of formula I according to claim 1, wherein X is —S—, $R_8$ is $C_1$-$C_4$alkylene, and $R_9$ is $C_1$-$C_4$alkyl, and q is 0.

* * * * *